United States Patent [19]

Wallace et al.

[11] Patent Number: 5,886,190
[45] Date of Patent: Mar. 23, 1999

[54] RAPID SYNTHESIS AND USE OF 18F-FLUOROMISONIDAZOLE AND ANALOGS

[76] Inventors: Sidney Wallace, 3324 Pittsburg, Houston, Tex. 77005; David J. Yang, 1123 Spinnaker Way, Sugarland, Tex. 77478; Abdallah Cherif, 5802 Ariel St., Houston, Tex. 77074

[21] Appl. No.: 979,051

[22] Filed: Nov. 26, 1997

Related U.S. Application Data

[62] Division of Ser. No. 624,574, Apr. 4, 1996, Pat. No. 5,728,843, which is a continuation of Ser. No. 131,484, Oct. 4, 1993, abandoned.

[51] Int. Cl.$^6$ .................................................. C07D 233/91
[52] U.S. Cl. .................................... 548/332.5; 548/341.4; 548/341.5
[58] Field of Search ................ 548/332.5, 341.4, 548/341.5

[56] References Cited

U.S. PATENT DOCUMENTS

| | | | |
|---|---|---|---|
| 3,549,653 | 12/1970 | Braman et al. | 548/311.1 |
| 3,689,502 | 9/1972 | Scollick et al. | 260/309 |
| 3,882,136 | 5/1975 | Levon | 260/299 |
| 3,997,572 | 12/1976 | Cusic et al. | 260/281 |
| 4,156,008 | 5/1979 | Heeres | 548/311.1 X |
| 4,282,232 | 8/1981 | Agrawal | 424/267 |
| 4,456,610 | 6/1984 | Hofheinz et al. | 424/273 |
| 4,462,992 | 7/1984 | Agrawal et al. | 424/180 |
| 4,632,932 | 12/1986 | Krämer et al. | 514/383 |
| 5,073,639 | 12/1991 | Suto | 548/339 |
| 5,192,778 | 3/1993 | Kodaka et al. | 514/341 |
| 5,235,057 | 8/1993 | Kleemann et al. | 546/269 |
| 5,387,409 | 2/1995 | Nunn et al. | 424/1.75 |
| 5,401,490 | 3/1995 | Wiebe et al. | 424/1.73 |
| 5,728,843 | 3/1998 | Wallace et al. | 548/327.5 |

FOREIGN PATENT DOCUMENTS

| | | | |
|---|---|---|---|
| 0319057 | 6/1989 | European Pat. Off. | 548/311.1 |
| 2095236 | 9/1982 | United Kingdom | 548/311.1 |
| WO 83/02774 | 8/1983 | WIPO | 548/311.1 |

OTHER PUBLICATIONS

Cherif et al., "2–Nitroimidazole Anaologues: Synthesis and Non Invasive Detection of Hypoxic Cells," *Proceedings of the American Association for Cancer Research*, 36:210, Toronto, Ontario, Canada, Mar. 1995.

Cherif et al., "Development of New Markers for Hypoxic Cells: [$^{131}$I]Iodomisonidazole and [$^{131}$I]odoerythronitroimidazole," *Journal of Drug Targeting*, 4:31–39, 1996.

Cherif et al., "Iodoerythronitroimidazole(Ietnim): Evaluation as a New Hypoxic Cell Radiosensitizer," *Pharmaceutical Research*, 12(9):S133, Abstract No. MNPC 5042, 1995.

Cherif et al., "Rapid Synthesis of 3-[$^{18}$F] Fluoro–1(2'–Nitro–1'–Imidazolyl)–2–Propanol ([$^{13}$F]Fluoromisonidazole)," *Pharmaceutical Research*, 11(3):466–469, 1994.

Nunn et al., "Nitroimidazoles and Imaging Hypoxia," *European Journal of Nuclear Medicine*, 22(3):265–280, 1995.

Yang et al., "Development of F–18–labeled Fluoroerythronitroimidazoles a PET Agent for Imaging tumor Hypoxia," *Radiology*, 194(3):795–800, Mar. 1995.

Lim et al., "An efficient radiosynthesis of [$^{18}$F]Fluoromisonidazole," *Appl. Radiat. Isto.*, 44(8):1085–1091, 1993.

Hwang et al., "No–carrier–added synthesis of 3-[$^{18}$F] Fluoro–1–(2–nitro–limidazolyl)–2–propanol. A potential PET agent for detecting hypoxic but biable tissues," *Appl. Radiat. Isot.*, 40(2):117–126, 1989.

Greene, "Protective Groups in Organic Synthesis," John Wiley & Sons, New York, pp. 50–55, 1981.

Grierson et al., "A Radiosynthesis of Fluorine–18 Fluoromisonidazole", *J. Nucl. Med.* 30(3):343–50, 1989.

*Primary Examiner*—Johann Richter
*Assistant Examiner*—Dominic Keating
*Attorney, Agent, or Firm*—Arnold White & Durkee

[57] ABSTRACT

The present invention involves a rapid synthesis of $^{18}$F-FMISO and analogs thereof. New precursors such as 1-(2'-nitro-1'-imidazolyl)-2-0-acetyl-3-0-tosylpropanol, glycerol-1,3-ditosylate-2-0-acetylate, 1-(2'-nitro-1'-imidazolyl)-2,3-0-diacetyl-4-0-tosylbutanol and threitol 1,4-di-tosylate-2,3-0-diacetylate, are also important aspects of the invention.

A further aspect of the invention is the development of a hydrophilic PET ligand to image tumor hypoxia. Erythrotosyl analogue of 2-nitroimidazone (Ts-ETNIM) was prepared from a mixture of 2-nitromidazole, ditosylthreitol and cesium carbonate at 60° C. for 1 hr. Ts-ETNIM was isolated at 70% yield. [$^{18}$F]fluoroerythronitroimidazole (FETNIM) was then prepared from Ts-ETNIM and K$^{18}$F/kryptofix®. The yield for [$^{18}$F]FETNIM was 26–30% (60 min, decay corrected). Results of biodistribution and PET studies indicate that [$^{18}$F]FETNIM has the potential to detect tumor hypoxia and is indicated to be less neurotoxic.

5 Claims, 9 Drawing Sheets

Na$^{131}$I/acetone

H$^+$/H$_2$O

IC

RAPID SYNTHESIS AND USE OF 18F-FLUOROMISONIDAZOLE AND ANALOGS

This application is a divisional of application Ser. No. 08/624,574 filed Apr. 4, 1996 now U.S. Pat. No. 5,728,843 which is a national stage entry of PCT/US 94/11246 filed Oct. 4, 1994 which is a continuation in part of U.S. application Ser. No. 08/131,484 filed Oct. 4, 1993 now abandoned.

BACKGROUND OF THE INVENTION

Field of the Invention

Tumor cells are more sensitive to radiation in the presence of oxygen than in its absence Powers et al., 1963). Even a small percentage of hypoxic cells within a tumor could limit response to radiation (Hall, 1988). Hypoxic radioresistance has been demonstrated in many experimental and animal tumors and hypoxia has been directly demonstrated in certain tumor types in man (Moulder et al., 1984; Peters et al., 1982). The occurrence of hypoxia in human tumors has in most cases been inferred from histologic findings and from evidence of hypoxia in animal tumor studies. In vivo demonstration of hypoxia has required tissue measurements with oxygen electrodes and the invasiveness of this technique has limited its application. Most attempts to increase the radiosensitivity of tumors by administration of chemical radiosensitizers have not been successful (Gatenby, et al., 1988; Kayama et al., 1991; Maor et al., 1981). However, there has been no clinically applicable means of demonstrating tumor hypoxia and it has not been possible to identify the patients who could potentially benefit from radiosensitizing therapy. Potential advantages of neutrons over more conventional radiation include a lesser dependence on oxygenation of the tumor and a lower variability of cell neutron sensitivity around the cell cycle.

3-[$^{18}$F]Fluoro-1-(2'-nitro-1'-imidazoyl)-2-propanol ($^{18}$F-fluoromisonidazole; FMISO) has been used with positron emission tomography (PET) to differentiate metabolically active hypoxic tumor from well-oxygenated metabolically active tumor. $^{18}$F-FMISO is metabolized by intracellular nitroreductases and acts as a competing electron acceptor at low oxygen levels. The $^{18}$FMISO is reduced and subsequently incorporated into metabolically active hypoxic cells by covalent bonding to various macromolecules. Recent studies have shown that PET, in view of its ability to monitor cell oxygen content through $^{18}$F-FMISO, has a high potential to predict treatment response. (Koh et al., 1992; Valk et al., 1992; Martin et al., 1989; and Rasey et al., 1989.)

Assessment of tumor hypoxia with $^{18}$F FMISO prior to radiation therapy provides a rational means of selecting patients for treatment with chemical radiosensitizing drugs. Such selection of patients permits more accurate evaluation of radiosensitizing drugs, since their use could be limited to patients with hypoxic tumors, who could potentially benefit. In addition, it is possible to differentiate radiotherapy modalities (neutron versus photon radiotherapy) by correlating [$^{18}$F]FMISO results with tumor response.

The synthesis of [$^{18}$F]FMISO reported by others showed no resemblance to the present inventive methods. Most studies used a two-part, two-step synthetic procedure, whereas the precursor of the present invention has a nitroimidazole moiety. Although there is a great demand in PET for [$^{18}$F]FMISO, a simple and efficient synthesis to produce sufficient radioactivity of [$^{18}$F]FMISO is difficult. Prior studies used [$^{18}$F]epifluorohydrin to react with 2-nitroimidazole (Hwang et al., 1989; Jerabek et al., 1986; Grierson et al., 1989). The reaction takes a longer time (90 min.) and provides a lower radiochemical yield. One aspect of the present invention concerns a more rapid synthesis of [$^{18}$F]FMISO.

Three classes of agents have found practical use for therapy against hypoxia tumors (Hall, 1994). These are (1) radiosensitizers of hypoxic cells, (2) chemopotentiation agents and (3) bioreductive drugs. Radiosensitizers are chemical or pharmacologic agents that increase the lethal effects of radiation when administered in conjunction with it. Nitroimidazoles were reported to potentiate the cytotoxic effects when combined with other chemotherapeutic agents (e.g. cisplatin, bleomycin, cyclophosphamide and nitrosourea). Several clinical trials are in progress combining a radiosensitizer with alkylating agents. It would increase the efficiency of chemotherapy if the hypoxia component could be identified by a labeled tracer prior to the therapy. Bioreductive drugs are not radiosensitizers, yet, these drugs are reduced intracellularly in hypoxia cells to form active cytotoxic agents. Three drugs are primarily used in clinical trials. These drugs are mitomycin C, triapazamine (SR4233) and dual-function nitroheterocyclic compounds (RB6145).

Two nitroimidazole analogues (misonidazole and etanidazole) are potent radiosensitizers. In clinical trails, patients with high hemoglobin levels and cancer of the pharynx showed a great benefit from the addition of these analogues (Hall, 1994). However, the dose-limiting toxicity was found to be peripheral neuropathy that progressed to central nervous system toxicity if drug administration was not stopped. This neurotoxicity prevented the use of the drug at adequate dose levels throughout multifraction treatments.

Therefore, it is necessary to develop a more hydrophilic agent than misonidazole. This would allow the agent to have shorter half-life in vivo and, be expected to show less neurotoxicity. Another aspect of the present invention is the synthesis and evaluation of a new 2-nitroimidazole analogue which is more hydrophilic than FMISO and misonidazole. The synthetic scheme is shown in FIG. 6.

SUMMARY OF THE INVENTION

The present invention includes a first description of new compounds including: 1-(2'-nitro-1'-imidazolyl)-2-O-acetyl-3-O-tosylpropanol; glycerol-1,3-ditosylate-2-O-acetylate; 1-(2'-nitro-1'-imidazolyl)-2,3-acetyl-4-O-tosylbutanol; and threitol 1,4-di-tosylate-2,3-O-di-acetylate.

The present invention also involves a method for preparing 1-(2'-Nitro-1'-imidazolyl)-2-O-acetyl-3-O-tosylpropanol comprising reacting glycerol-1,3-ditosylate-2-O-acetylate with 2-nitroimidazole. This reaction is preferably in dimethylformamide in combination with cesium carbonate. Preferable conditions for this reaction are at a temperature of 50° C. and for a time of about 1 hour. The present invention also involves a method for preparing $^{18}$F-fluoromisonidazole comprising reacting 1-(2'-nitro-1'-imidazolyl)-2-propanol with $^{18}$F complexed with 4,7,13,16, 21,24-hexaoxa-1,10-diazabicyclo[8,8,8]hexacosane or the like. This reacting is preferably in an acetonitrile solvent. Reaction conditions here are preferably from about 90° C. to about 100° C.

Methods of the present invention include: A method for preparing 1-(2'-nitro-1'-imidazolyl)-2,3-acetyl-4-O-tosylbutanol comprising reacting threitol-1,4-di-tosylate-2, 3-O-acetylate with 2-nitroimidazole. Also part of the present invention is a method for preparing a $^{18}$F- fluoromisonidazole butanol analogue useful for PET imaging and localization of hypoxia tissue. This method comprises reacting 1-(2'-nitro-1'-imidazolyl)-2,3-acetyl-4-O-tosylbutanol with $^{18}$F complexed with 4,7,13,16,21,24-hexaoxo-1,10-diazabicyclo(8,8,8)hexacosane or the like. The present invention also comprises a method for preparing $^{131}$I-iodomisonidazole comprising reacting 1-(2'-nitro-1'-imidazolyl)-2-acetyl-3-O-tosylpropanol with a salt of $^{131}$I such as Na$^{131}$I.

Another aspect of the present invention is the preparation of a more hydrophilic analogue of misonidazole, [$^{18}$F] fluoroerythro-2-nitroimidazole. This compound is prepared from a novel precursor, (2'-nitro-1'-imidazolyl)-2,3-isopropylidene-4-tosylbutanol.

The method for preparing (2'-nitro-1'-imidazolyl)-2,3-isopropylidene-4-tosylbutanol comprises reacting 1,4-ditosyl-2,3-isopropylidene-D-threitol with 2-nitroimidazole, and preferably the reacting is in dimethylformamide, and preferably the reacting is in the presence of cesium carbonate. The reacting is also preferably at about 60° C. for about 1 hour.

A further aspect of the invention is a method for preparing [$^{18}$F]fluoroerythro-2-nitroimidazole comprising reacting (2'-nitro-1'-imidazolyl)-2,3-isopropylidene-4-tosylbutanol with $^{18}$F complexed with 4,7,13,16,21,24-hexaoxa-1,10-diazabicyclo[8,8,8]hexacosane. In this method, the reacting is preferably in acetonitrile.

An embodiment of the present invention is a method of use of [$^{18}$F]fluoroerythro-2-nitroimidazole for assessing tumor hypoxia. The method of use preferably comprises administering to a patient an effective amount of [$^{18}$F] fluoroerythro-2-nitroimidazole and subjecting the patient to positron emission tomography or single photon emission computed tomography.

DETAILED DESCRIPTION OF THE PREFERRED EMBODIMENTS

The present precursors for the preparation of [$^{18}$F]FMISO or its butanol analog are of value clinically and scientifically. The precursor for [$^{18}$F]FMISO is 1-(2'-nitro-1'-imidazolyl) -2-O-acetyl-3-O-tosylpropanol. Such a precursor can be radiolabeled in a short time with $^{18}$F (t½=(109.7 min.), $^{123}$I (t½=13.3 hours) or $^{131}$I. The first two radioisotopic ligands are useful to detect hypoxic tumor volume by positron emission tomography (PET) and single photon emission computed tomography (SPECT).

Figure 1:
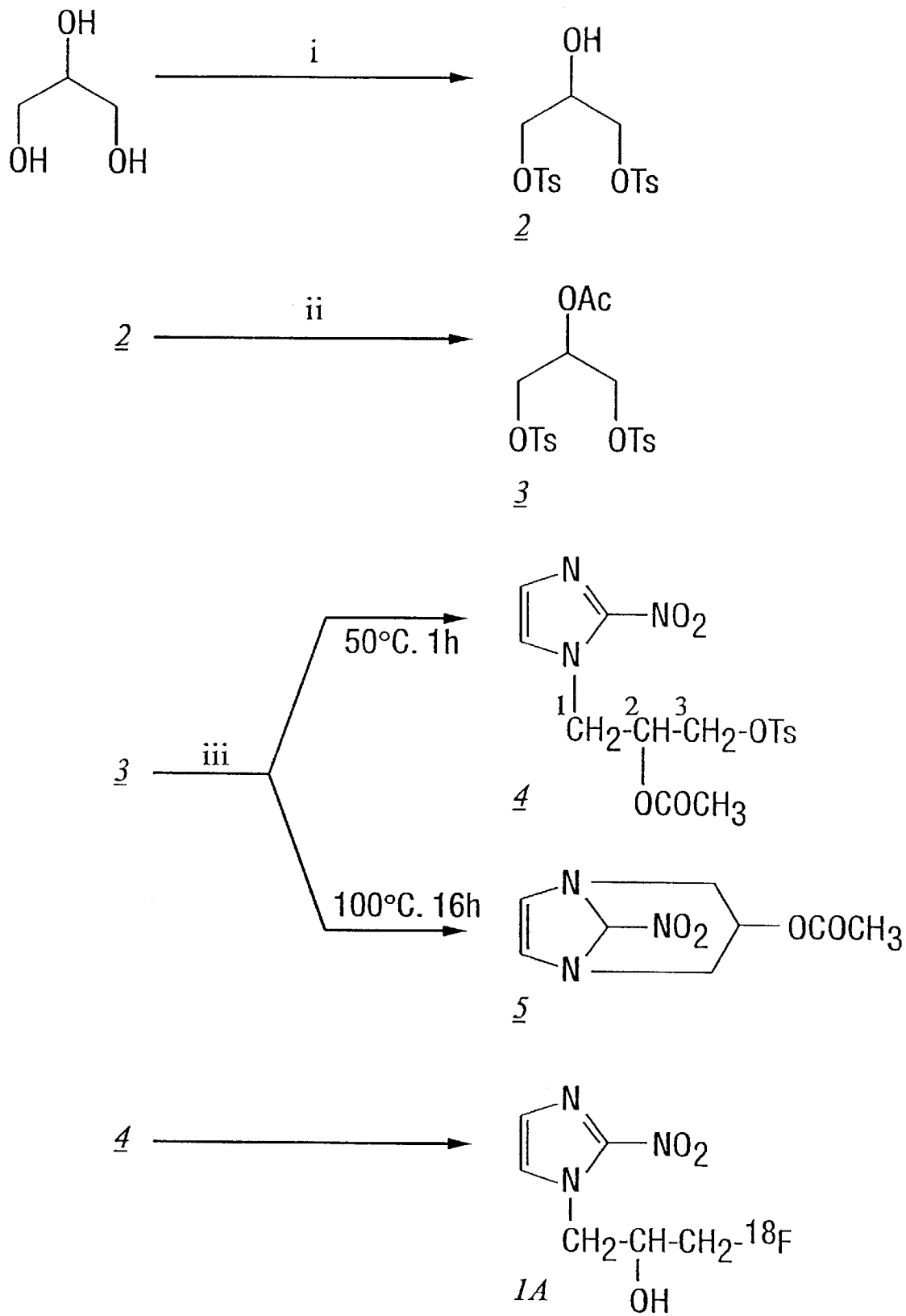
FIG. 1 schematically shows the synthesis of [$^{18}$F] fluoromisonidazole and its analogue.

[$^{18}$F]FMISO was prepared as schematically shown in FIG. 1. Glycerol-1,3-ditosylate (compound 2) was obtained by treating glycerol with tosyl chloride according to a previously reported method (Benbouzid et al., 1988). Compound 3 (2-acetyl glycerol-1,3-ditosylate) was prepared by reacting glycerol-1,3-ditosylate with anhydrous acetic anhydride and BF$_3$.etherate (yield 100%). In a mixture of compound 3, 2-nitroimidazole and Cs$_2$CO$_3$ in dry DMF at 50° C., compound 4 [1-(2'-nitro-1'-imidazolyl)-2-O-acetyl-3-O-tosylpropanol] was prepared. (When this reaction was carried out at 100° C. for 16 hr, the undesired compound 5 resulted.) HPLC showed the retention time of compound 4 to be 9.83 minutes (UV 310 nm, C-18 reverse phase column eluted with H$_2$O:MeOH; 0–80% at a flow rate of 1.5 ml/min.

The butanol FMISO analog was analogously prepared.

Compound 1 ([$^{18}$F]fluoromisonidazole) is prepared just prior to use by reacting compound 4 with [$^{18}$F]/ KRYPTOFIX® 222.

Figure 2:
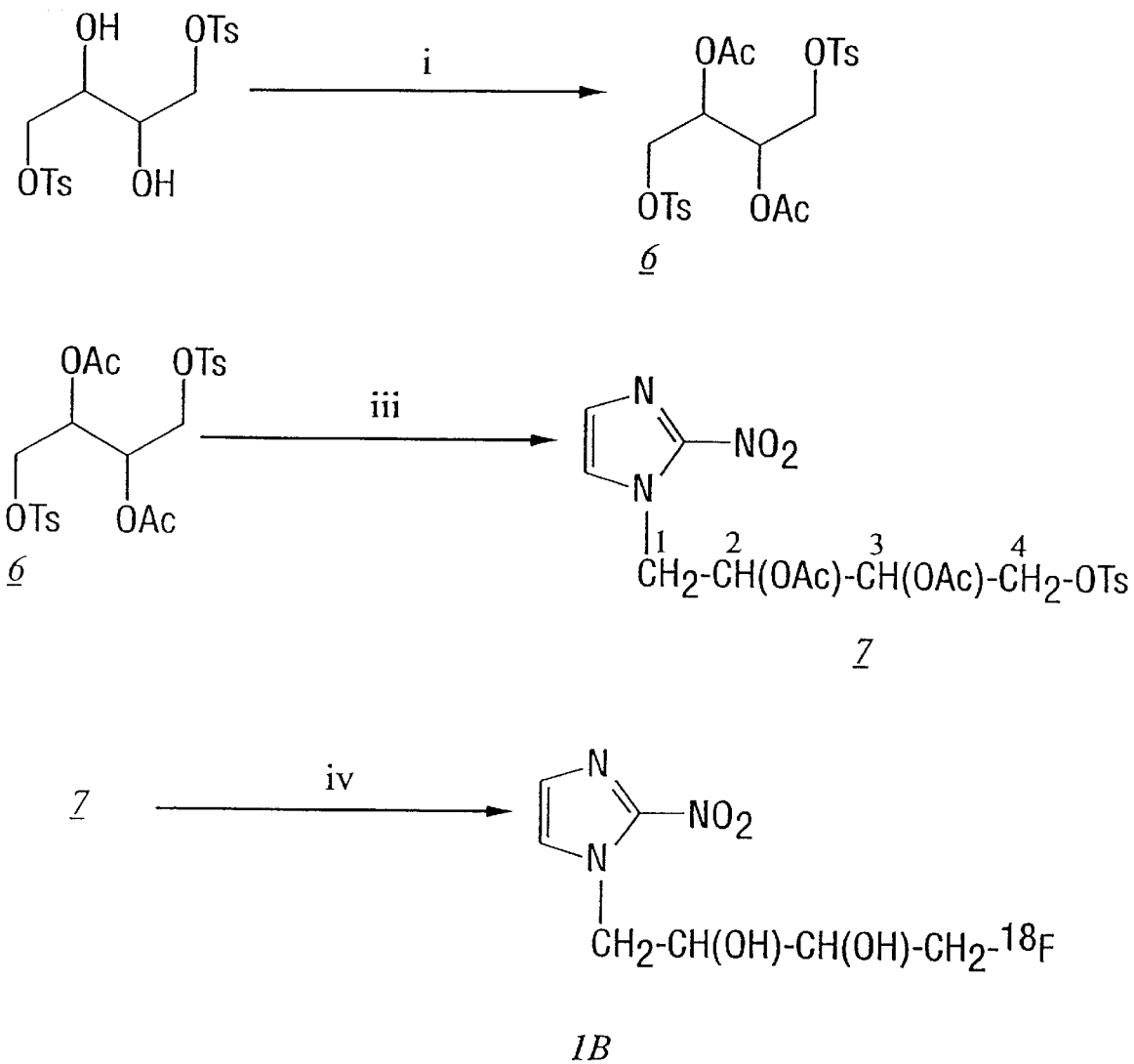
FIG. 2 schematically shows the synthesis of -(2'-nitro-1'-imidazolyl)-2,3-O-acetyl-4-O-tosyl butanol.

Reagents and conditions for the steps in FIG. 1 and FIG. 2: i) TsCl (2eq), Pyridine, 0° C., 48 h (90%); ii) Ac$_2$O (1.5 eq) BF$_3$.Et$_2$O (in anhydrous ether, 0° C., 30 min (100%), iii) 2-nitroimidazole, (0.9 eq), Cs$_2$CO$_3$ (0.9 eq), DMF, 50° C., 1 h (48%); iv) [$^{18}$F]/KRYPTOFIX , CH$_3$CN, 95° C., 10 min., H$^+$, 90° C., 5 min. (12–18%).

Accomplished syntheses of misonidazole and misonidazole analogue precursors, $^{18}$F-fluoromisonidazole (FMISO), [$^{131}$I]iodomisonidazole ($^{131}$I-IMISO) and $^{18}$F-fluoromisonidazole analogues are described in the Examples below.

Figure 6:
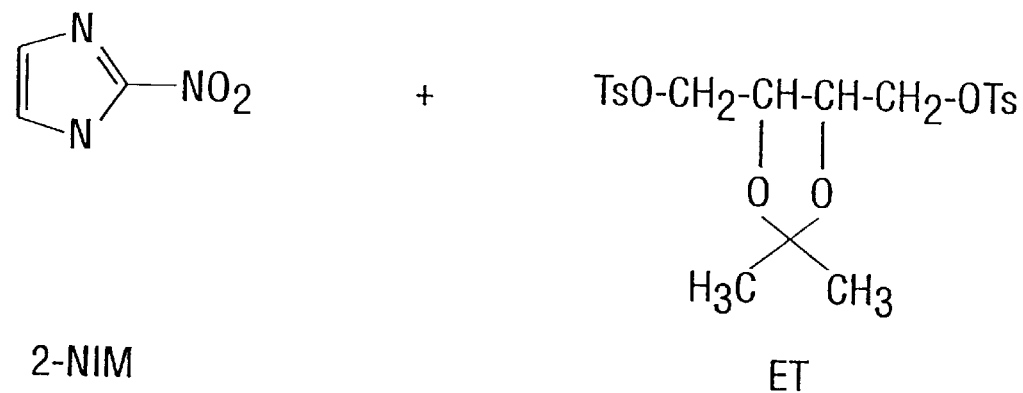
FIG. 6 schematically shows the synthesis of [$^{18}$F] FETNIM.
Figure 6:
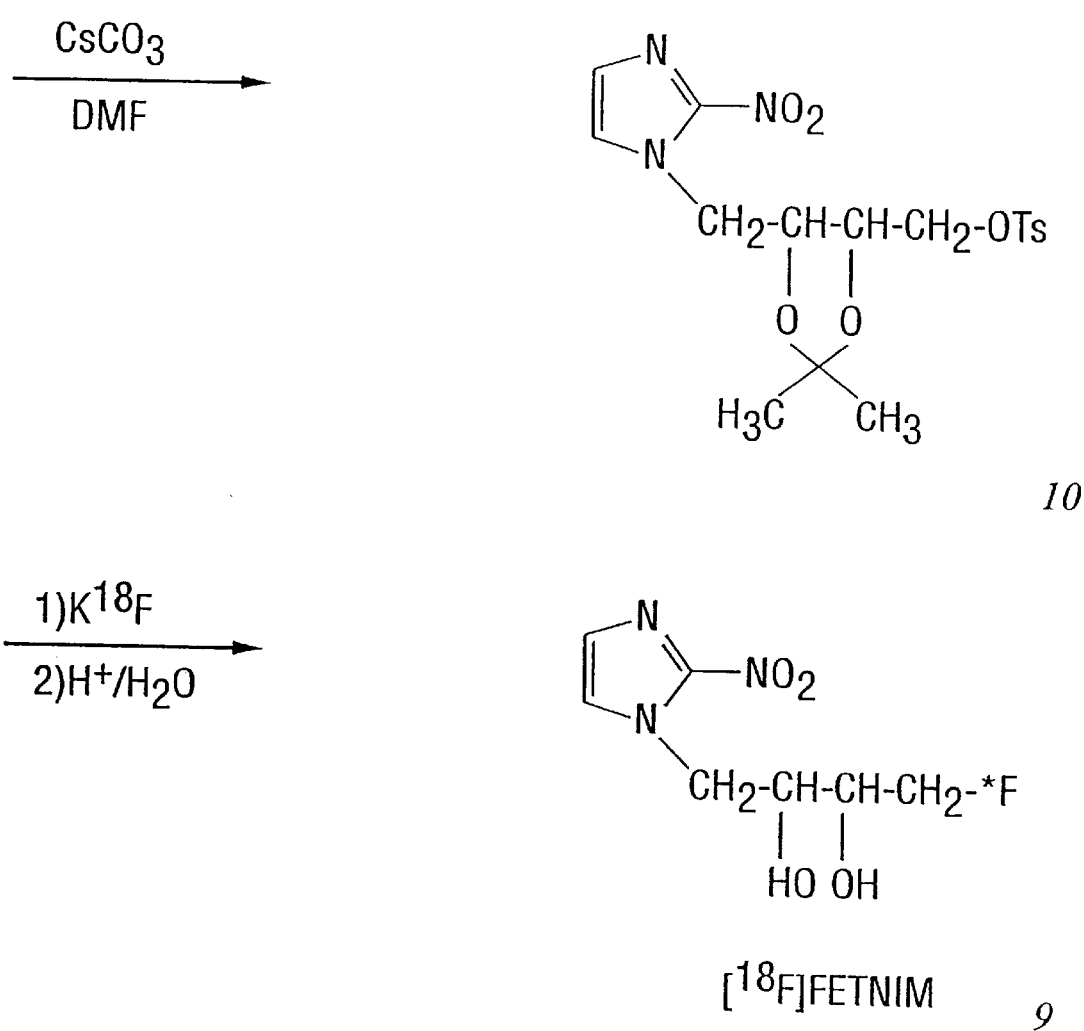

The synthesis scheme for [$^{18}$F]FETNIM is depicted in FIG. 6. Biodistribution studies of [$^{18}$F]FETNIM were performed at 1, 2 and 4 hours in mammary tumor-bearing rats (10 µCi, iv, N=3/time interval). Autoradiograms were performed at 1 hour postinjection of [$^{18}$F]FETNIM, and a comparison has been made with [$^{18}$F]fluoromisonidazole (FMISO). Intratumoral oxygen tension measurements were performed using the Eppendorf computerized histographic system. Twenty to twenty-five pO$_2$ measurements along each of 2 to 3 linear tracks were performed at 0.4 mm intervals on each tumor. PET imaging studies of [$^{18}$F] FETNIM were performed in rabbits bearing V2 tumors (N=3, 4 mCI, iv) which were located on the right leg.

Biodistribution of [$^{18}$F]FETNIM at 1, 2 and 4 hours showed tumor/blood count density ratios of 2.29±0.599, 2.41±0.567 and 8.02±2.420; tumor/muscle ratios of 0.66±0.267, 2.11±0.347 and 5.92±2.240, respectively. Bone uptake did not alter significantly. Autoradiograms indicated that [$^{18}$F]FETNIM and [$^{18}$F]FMISO could differentiate hypoxic versus necrotic regions in the tumor. The tumor oxygen tension, measured by an oxygen needle probe; was 3.2–6.0 mmHg. PET imaging studies indicated that the hypoxic tumor could be visualized at 1 hour postinjection.

The data disclosed herein indicate that [$^{18}$F] FETNIM and [$^{18}$F]FMISO are selective to hypoxic cells. However, [$^{18}$F] FETNIM appears to be more hydrophilic than [$^{18}$F]FMISO as evidenced from the autoradiogram and chemistry. Therefore, [$^{18}$F]FETNIM has the potential to be used as a diagnostic tool and as a follow-up for conventional therapy or chemotherapy of hypoxic tumors. Other useful applications of this compound would be in the diagnosis of brain ischemia (acute stroke), nasopharyngeal cancer, inflammation and cardiac infarction. Additionally, because of the selectivity and specificity of [$^{18}$F]FETNIM, labeling erythronitroimidazole with a high dose of $^{131}$I would allow for radionuclide therapy of hypoxic tumors.

In summary, a simple and efficient synthetic method to produce sufficient radioactivity of [$^{18}$F]fluoroerythronitroimidazole, a new PET agent for imaging tumor hypoxia, has been prepared. PET imaging studies, autoradiograms and biodistribution of this compound indicate that [$^{18}$F]fluoroerythronitroimidazole is selective to hypoxic cells, chemically stable and more hydrophilic than misonidazole. It is thus a useful compound for the evaluation of hypoxic tumors. The diagnostic information obtained from [$^{18}$F]FETNIM would be important for the follow-up therapy of patients with hypoxic tumors.

EXAMPLE 1

Experimental Section (Applying to these Examples)

Nuclear magnetic resonance (NMR) spectra ($^1$H and $^{13}$C) were recorded at ambient temperature on an IBM-Bruker Model NR/200 AF spectrometer in the Fourier transform mode in CDC13 with tetramethylsilane as an internal reference. Chemical shifts (d) are reported in parts per million (ppm) and coupling constants (J) in hertz. Mass spectral analyses were conducted at the University of Texas, Health Science Center at Houston, Texas. The mass data was obtained by fast-atom bombardment on a Kratos MS50 instrument. The elemental analyses were conducted at Galbraith Laboratories Inc. (Knoxville, Tenn.). High resolution mass spectroscopy (HRMS) was performed at the Midwest Center for Mass Spectrometry (Lincoln, Nebr.). All chemical reactions were conducted in dry glassware and were protected from atmospheric moisture. Solvents were dried over freshly activated (300° C., 1 h) molecular sieves (type 4A). The homogeneity of the products was determined by ascending thin-layer chromatography (TLC) on silica-coated glass plates (silica gel 60 F 254, Merck) with mixtures of CHCl$_3$-MeOH as the eluting solvent. Preparative separations were performed by column chromatography on silica gel (Merck, 230–400 mesh) with mixtures of CHCl$_3$-MeOH as eluant.

EXAMPLE 2

Synthesis of qlycerol-1,3-ditosylate (Compound 2)

Compound 2 was synthesized according to the previous reported method with modifications (Benbouzid et al., 1988). p-Toluenesulfonyl chloride (10.29 g, 54 mmol) dissolved in dry pyridine was added to a stirred solution of anhydrous glycerol (2.48 g, 27 mmol) in dry pyridine (30 ml at 0° C.). The solution was added slowly and left to react for 44 hours in the refrigerator (0°–3° C.). The pink mixture was poured over crushed ice and acidified with concentrated HCl. The organic layer was separated and the aqueous layer was washed with methylene chloride (2×50 ml). The combined organic extracts were washed successively with 2N HCl (2×10 ml) and distilled water (2×10 ml) and dried over anhydrous Na$_2$SO$_4$. The filtrate was evaporated and the residual crude product was purified by column chromatography on silica gel to afford Compound 2 as an oil: 9.72 g (24.3 mmol) yield 90%. $^1$H NMR [Chemical shift (d), multiplicity, coupling constant (Hz), number of protons, atom]: 7.75 (d; J=8.2 Hz; 4H, Har.); 7.35 (d; J=8.2 Hz; 4H; Har.); 4.1 (bs; 4H; H$_{1,3}$); 3.35 (bs; 1H; H$_2$); 2.4 (s; 6H; 2CH$_3$). $^{13}$C NMR (ppm): 145 (C ar.); 131.7 (C ar.); 129.7 ( CH ar.); 127.6 (CH ar.); 69.3 (C$_{1,3}$); 66.7 (C$_2$); 21.2 ( CH$_3$) Satisfactory $^1$H and $^{13}$C NMR data as well as mass spectral data were recorded for this compound. These spectra were consistent with the structures shown in FIG. 1.

EXAMPLE 3

Synthesis of Glycerol-1,3-ditosylate-2-O-acetylate (compound 3)

Glycerol-1,3-ditosylate (5 g, 12.5 mmol) was added dropwise, while stirring 5 minutes at about 0° C., to a solution of acetic anhydride (2 ml, 20 mmol) and BF$_3$.etherate (1.0 ml) in anhydrous ether (50 ml). The reaction mixture was stirred for 10 minutes, washed successively with 25%. sodium acetate solution (10 ml) and water (2×15 ml), and then dried over anhydrous sodium sulfate. The solvent was evaporated to yield glycerol-1,3-ditosylate-2-O-acetylate as a white solid (5.48 g, 12.4 mmol). The structure of the product was confirmed by $^1$H-NMR $^{13}$C-NMR, mass spectral data and elemental analysis. These spectra were consistent with the structure of glycerol-1,3-ditosylate-2-O-acetylate shown in FIG. 1. $^1$H NMR: 7.8 (d; J=8.0 Hz; 4H; Har.); 7.3 (d; J=8.0 Hz; 4H; Har.); 5.05 (t; J-4.8 Hz; 1H; H$_2$); 4.1 (d; J=4.8 Hz; 4H; H$_{1,3}$); 2.4 (s; 6H; 2CH3ar.); 1.8 (s; 3H; CH$_3$ ac.). $^{13}$C NMR (ppm): 169.6 ( COCH$_3$); 145.3 (C ar.); 132.2 (C ar.); 130 (CH ar.); 127.9 ( CHar.); 68.1 (C$_2$); 66.5 (C$_{1,3}$); 21.6 (CH$_3$ ar.); 20.5 (OCO CH$_3$). mass [FAB, (C$_{19}$H$_{22}$S$_2$O$_8$)$^+$] m/z: 441 (M$^+$, 5%); 383 (M$^+$—OCOCH$_3$, 4%); 271 (M$^+$-tosylate, 100%), 229 (M$^+$+ 1-tosylate —COCH$_3$; 3%). Anal. Calc. (C$_{19}$H$_{22}$S$_2$O$_8$) : C: 51.58, H:4.97 Found: C:51.50 H:4.93.

EXAMPLE 4

Synthesis of 1-(2'-Nitro-1'-imidazolyl)-2-O-acetyl-3-O-tosvlpropanol (Compound 4)

A mixture of glycerol-1,3-ditosylate-2-O-acetylate (0.44 g, 1 mmol), 2-nitroimidazole (0.1 g, 0.9 mmol) and cesium carbonate (0.29 g, 0.9 mmol) in 10 ml of dry DMF, through which argon was bubbled for 10 minutes. The mixture was heated at 50° C. for 1 hour. The mixture was then cooled and DMF was carefully removed under reduced pressure. The residue was taken up in ethyl acetate and filtered. Removal of ethyl acetate in vacuo gave a yellow oil which was chromatographed on silica gel eluted with 50–67% ethyl acetate/petroleum ether to afford 1-(2'-Nitro-1'-imidazolyl)-2-O-acetyl-3-O-tosylpropanol as a white solid (0.17 g, 0.43 mmol), yield 48%. This was dried in vacuo and stored at 0° C. The structure of compound 4 was confirmed by $^1$H-NMR, $^{13}$C-NMR, and mass spectral data. The spectra were consistent with the structure of 1-(2'-nitro-1'-imidazolyl)-2-O-acetyl-3-O-tosylpropanol shown in FIG. 1. HPLC showed the retention time of this compound to be 9.83 minutes (UV 310 nm, C-18 reverse phase column, eluted with water/methanol 0–80% at a flow rate of 1.5 ml/min). However, if the reaction was heated at 100° C. for 16 hours, a major byproduct (Compound 5) was isolated.

Compound 4: IR (Nujol) (cm$^{-1}$): 1760; 1610; 1560; 1500; 1480; 1300; 1240; 1200. $^1$H NMR: 7.8 (d; 2HJ=8.1 Hz; 2Har), 7.4 (d; 2H; J=8.1 Hz; 2Har), 7.1 (d; 2H; J-2.9; H-imidazolyl), 5.3 (m; 1H; H$_2$), 4.85 (dd; 1H; J=14.4, 3.5 Hz; H$_{3a}$), 4.5 (dd; 1H; J=14.4, 8.4 Hz; H$_{3b}$), 4.2 (dd; 2H; J=5,4.1 Hz; H$_1$), 2.45 (s; 3H; CH3tosyl), 1.95 (s; 3H; CH3ac). $^{13}$C NMR (50 MHz), d(ppm): 169.3 (C=O), 145.6 (Car), 132 (Car), 130.1 (CHar), 129.9 (C-imidazolyl), 128.3 (CH-imidazolyl), 127.9 (CHar), 126.5 (CH-imidazolyl), 68.8 ($C_2$), 67.2 ($C_1$), 49.3 ($C_3$), 21.6 ($CH_3$tosyl), 20.3 ($CH_3$ac). HRMS calc. for $C_{15}H_{18}N_3SO_7$ 384.08655, Found 384.0869.

Compound 5: $^1$HNMR: 7.15 (2H, H-imidazolyl); 4.9 (S, 1H, H-imidazolyl); 4.8 (m, 1H, $H_2$); 4.2 (d, 4H, J=3.5 Hz); $H_{1,3}$), 2.1 (S, 3H, $CH_3$). $^{13}$CNMR; 171.1 (C=O), 127.7 (CH-imidazolyl); 68.2 (CH—$NO_2$); 65.4 ($C_2$) ; 52.8 ($C_{13}$), 21 ($CH_3$ ac). HRMS calcd for $C_8H_{12}N_3O_4$ 214.08278, found 214.0827.

EXAMPLE 5

Radiosynthesis of [$^{18}$F]FMISO (Compound 1)

[$^{18}$F]Fluoride was obtained from the cyclotron facility of the University of Texas M.D. Anderson Cancer Center as produced by proton irradiation of enriched [$^{18}$O]water in a small-volume silver target. An aliquot containing 250–500 mCi of $^{18}$F activity was combined with 26 mg of 4,7,13,16, 21,24-hexaoxa-1,10-diazabicyclo[8,8,8]hexacosane (KRYPTOFIX® 222) and anhydrous potassium carbonate (4.6 mg), heated under reduced pressure to remove [$^{18}$O] water, and dried by azeotropic distillation with acetonitrile (3×1.5 ml). The tosyl analogue of misonidazole (compound 4) (5 mg), prepared from 1,3-ditosyl-2-O-acetyl glycerol (compound 3) was dissolved in acetonitrile (1.5 ml), and the KRYPTOFIX® 222-fluoride complex added. The mixture was then warmed at 95° C. for 10 min. After cooling, the reaction mixture was passed through a silica gel Sep-Pak column (Whatman Lab, Clifton, N.J.) and eluted with ether (2×2.5 ml): The solvent was evaporated and the resulting mixture hydrolyzed with 1N HCl (2 ml) at 90° C. for 5 min. The resultant mixture was cooled under $N_2$ and neutralized with 2N NaOH (0.8 ml) and 1N $NaHCO_3$ (1 ml). The mixture was then processed by passage through a short alumina C-18 (Sep-Pak) column and a 0.22 µm Millipore filter, followed by 5 ml of 10% ethanol saline. Comparison with an $^1$H-NMR spectrum of the unlabeled fluoromisonidazole (FMISO) confirmed the structure. A yield of 20–40 mCi of pure product was isolated (12–18% yield, decay corrected) with end-of-bombardment (EOB) at 60–70 min. HPLC was performed on a C-18 Radial-Pak column, 8×100 mm, with pure water, using a flow rate of 1 ml/min. The no-carrier-added product corresponded to the retention time (4.8 min) of the unlabeled fluoromisonidazole under similar conditions. The radiochemical purity was greater than 95%. Under UV detection (310 nm), there are no other impurities. A radio-TLC scanner (Bioscan, Washington, DC) showed the retardation factor of 0.5 for the final product, using a silica gel plate G/UV 254, 5×20 cm (Whatman, Anaspec, Mich.) chloroform: methanol (7:3) eluant, which corresponded to unlabeled FMISO. In addition, KRYPTOFIX® 222 was not visualized (developed in iodine chamber) on the silica gel-coated plate using 0.1% v/v triethylamine in methanol as an eluant. The specific activity of FMISO was determined to be in the range of 1–2 Ci/µmol based upon UV and radioactivity detection of a sample of known mass and radioactivity. The identity and purity of [$^{18}$F]FMISO were confirmed by HPLC.

EXAMPLE 6

Half-life Test of [$^{18}$F]fluoromisonidazole

After the [$^{18}$F]fluoromisonidazole was prepared, an aliquot (10 µCi) of this radioactive product was counted on a gamma counter at various time intervals (30, 60, 120 min.). To assure the correct isotope ($^{18}$F) is incorporated into the nitroimidazole analogue, the radioactivity of the final product at different time intervals is counted and decay is corrected.

EXAMPLE 7

Sterility and Pyrogenicity

To demonstrate sterility, each batch of product is tested using Bactec culture vials with aerobic and anaerobic materials (NR6 and NR7) (Towson, Md.). An aliquot (0.3 ml) of the final solution is incubated in vials for 7 days at 37° C. Sterility is examined every day and assayed by visualizing the cloudiness of the solution. The ten samples tested have consistently been shown to be sterile.

To assure low or absent pyrogenicity, a LAL kit (Whittaker Bioproduct, Walkersville, Md.) is used. To prove drug solution does not enhance or inhibit the LAL test, we used three 1:1 dilutions (0.25 ml of drug solution to 0.25 ml of sterile water) to test pyrogenicity of each batch of product. Compared to standard solutions (12.5 Eµ/ml, 1.25 Eµ/ml and negative), the tested product solutions (ten samples) proved to be pyrogen-free (0 Eµ/ml) and did not interfere with the assay sensitivity.

EXAMPLE 8

Pharmacology and Toxicology Data

Pharmacology

Fluoromisonidazole (FMISO) has been shown to bind selectively to hypoxic cells in vitro and in vivo at radiobiologically significant oxygen levels. In patient studies, the hypoxic elements within a tumor volume was defined as regions with a threshold regional tumor to plasma ($^{18}$F-FMISO) ratio of ≧1.4 by 2 or more hours after injection.

The following Table summarizes the results of dosimetry calculation for radiation exposure to several hormonal tissues.

| Dosimetry: | Normal Tissue Dosimetry for $^{18}$F-FMISO | |
| --- | --- | --- |
| Organ | mrad/mCi ± SD | 7 mCi/70 Kg |
| Liver | 26.8 ± 9.7 | 190 mrad (n = 3) |
| Kidney | 25.8 ± 5.5 | 180 mrad (n = 3) |
| Muscle | 16.8 ± 7.9 | 120 mrad (n = 6) |
| Bladder | 81.5 ± 47 | 570 mrad (n = 2) |

Muscle is typical of most normal tissues; the total body musculature receives 120 mrem in a routine study for a 70 Kg male given the dose of 0.1 mCi/Kg. The liver and kidneys receive nearly twice the muscle dose, and the bladder wall about five times as much.

The data obtained from this study demonstrate the feasibility of using $^{18}$F-FMISO to detect hypoxia in human head and neck tumors. Clinical trials will determine whether a relationship exists between $^{18}$F-FMISO uptake and tumor radiation response.

Toxicity

Nitroimidazoles are chemotherapeutically important as antiprotozoal and antibacterial agents (Hoffer et al.). The most common side effect of MISO toxicity is peripheral sensory neuropathy of the hands and feet, characterized by mild to moderate paresthesias and loss of vibration sensitivity (McNeill et al.) . Others have reported convulsions after large single doses, and the development of toxicity, and encephalopathies, following small multiple doses (McNeill et al.) . The dose which affects the neurotransmitter system was in the range of 0.76 mg/g (in mice).

The specific activity of $^{18}$F-FMISO prepared is in the range of 1–3 Ci/µmol. The physical material will be in the range of 2–6µg per patient. This radiotracer dose is far below the toxicity dose. In addition, animal acute toxicity studies have been performed, rats (n=3) were administered 2 mCi/Kg as a single dose. All rats tolerated this dose without toxicity on longer follow-up periods (5 days). This dose is ten-fold higher than the dose thus far studied.

EXAMPLE 9

PET Imaging Studies Using [$^{18}$F]FMISO

PET imaging studies were performed on two patients with nasalpharyngeal cancer (NPC). Each patient was positioned supine in the scanner so that the detector rings would span the entire tumor region. A 20-min attenuation scan was performed with a 4 mCi $^{68}$Ge-ring source prior to tracer injection. After each patient had received 10 mCi of [$^{18}$F] FMISO, eight consecutive 15-min scans were taken. The total number of counts collected per scan was in the range of 15–30 million. Each patient was also administered [$^{18}$F] FDG to ascertain the tumor region.

Figure 3:
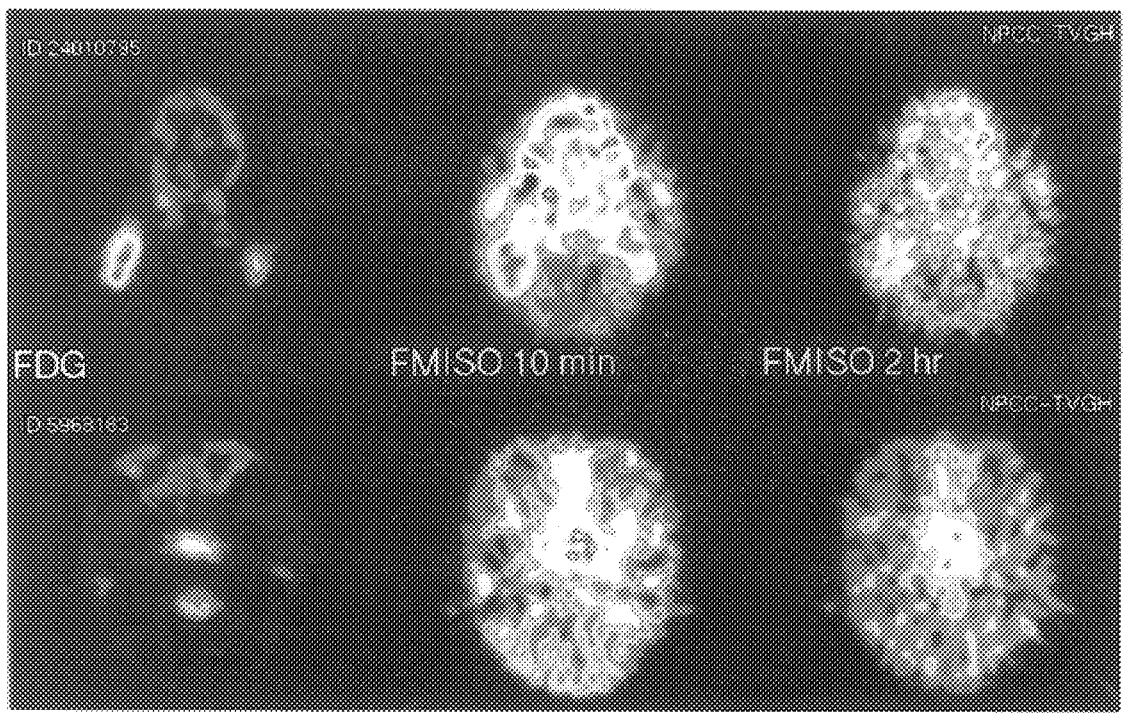
FIG. 3 shows a PET image of a patient with nasalpharyngeal cancer (NPC) after receiving 10 mCi each of ($^{18}$F) FMISO prepared according to the present invention.
Figure 4:
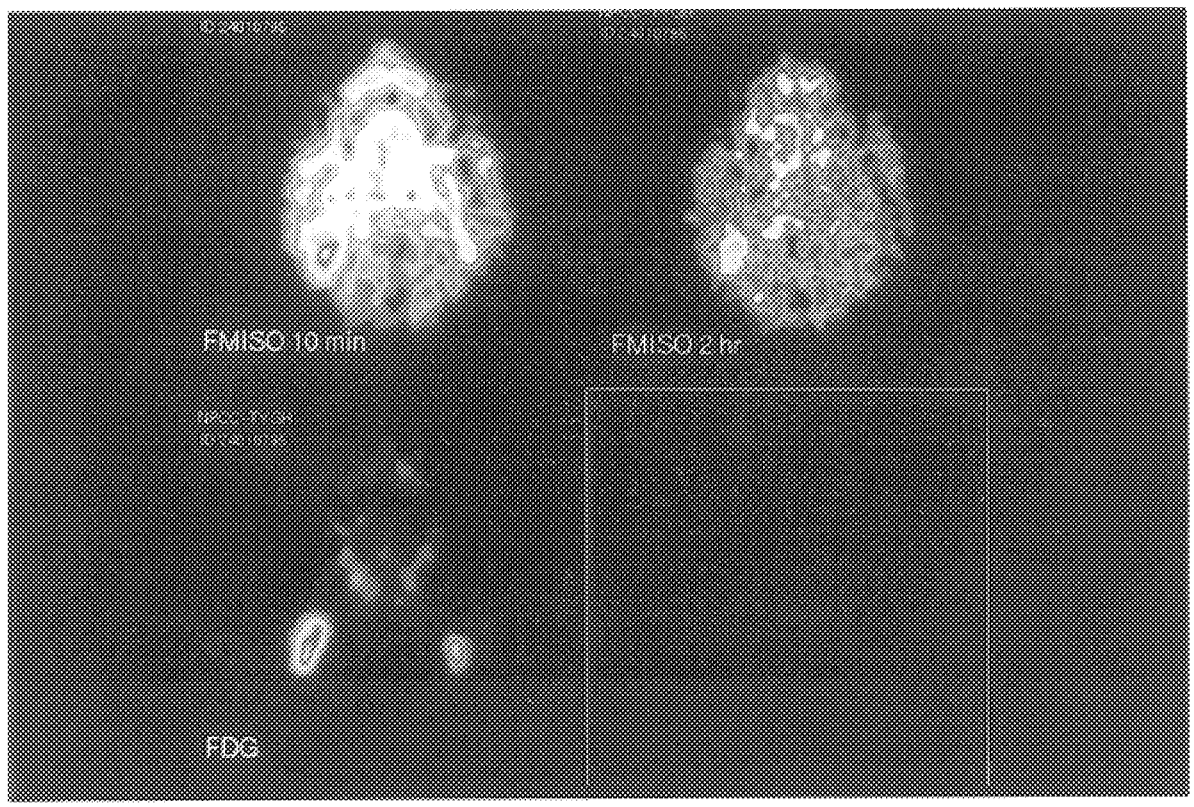
FIG. 4 shows a PET image of a second patient with nasalpharyngeal cancer (NPC) after receiving 10 mCi each of ($^{18}$F)FMISO prepared according to the present invention.
Figure 5:
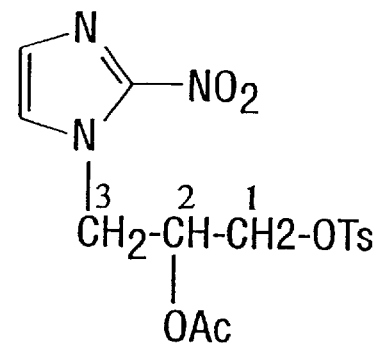
FIG. 5 schematically shows the radiosynthesis of ($^{131}$I) iodomisonidazole.
Figure 5:
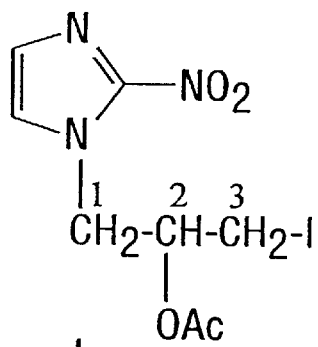
Figure 5:
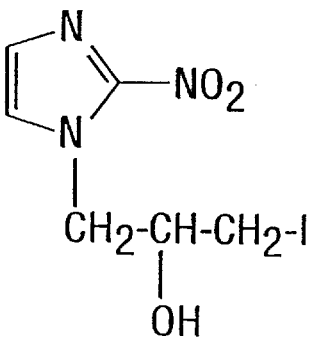

In the first patient, [$^{18}$F]FMISO showed tumor uptake in the lymph node region (see FIG. 3) suggesting the tumor metastasized to lymph node is hypoxia. In the second patient, the recurrent primary tumor is hypoxic (see FIG. 4). This study demonstrates that [$^{18}$F]FMISO is able to detect primary or metastatic hypoxic tumors.

EXAMPLE 10

Synthesis of L-Threitol-1,4-di-p-tosylate-2,3-O-diacetylate (Compound 6)

A solution of L-threitol 1,4-di-p-tosylate (1 g, 2.3 mmole) was added dropwise with stirring over 5 min. at room temperature, to a solution of acetic anhydride (3 ml, 31 mmole) and BF$_3$,etherate (0.2 ml) in anhydrous ether (20 ml). The reaction mixture was stirred for 10 min., washed successively with 25% sodium acetate solution (10 ml) and water (25 ml×2), and dried over anhydrous sodium sulfate. The solvent was evaporated, and the residue was distilled under reduced pressure to give the acetylated compound. Yield 94%. The structure of the desired compound was confirmed by $^1$H NMR, $^{13}$C NMR and mass spectral data. $^1$H NMR: 7.75 (d; J=8.3 Hz; 4H; Har.); 7.35 (d; J=8.3 Hz; 4H; Har.); 5.2 (t; J=3.2 Hz; 2H; H2, 3H); 4.2 (t; J=5 Hz; 4H; H1, 4); 2.5 (s; GH; 2CH$_3$ar.); 2.0 (s; 6H; 2CH$_3$ac.). $^{13}$C NMR: 169.5(O$\underline{C}$OCH3); 145.3 (C ar.); 132.2(C ar.); 129.9 (CH ar.); 127.9(Ch ar.); 68.3 (C2,3); 66.4 (C1, 4); 21.6 (CH$_3$ ar.); 20.4 (OCO$\underline{C}$H$_3$). MS [FAB, C22H26S2010)] m/z: 515(M$^+$ +1, 55); 455 (M$^+$—OCOCH$_3$, 8%); 342 (M$^+$-tosylate, 100%).

EXAMPLE 11

Synthesis of 1-(2'-Nitro-1'-imidazolyl)-2,3 -O-acetyl-4-O-tosylbutanol (Compound 8)

2-Nitroimidazole (100 mg, 0.88 mmole) was dissolved in DMF (1 ml), cesium carbonate (289 mg) was added and the reaction stirred for 5 min at room temperature. Threitol 1,4-di-p-tosylate 2,3-diacetate (1.1 eq., 431.5 mg, 0.97 mmole) was added last, and the reaction was stirred at 80° C. for 1 hour. The reaction was filtered and the DMF removed in vacuo. The residue was chromatographed on alumina eluted with ethyl acetate/petroleum ether. The structure of resultant 1-(2'-Nitro-1'-imidazolyl)-2,3-O-acetyl-4-O-tosylbutanol, the fluoromisonidazole butanol analog, was confirmed by $^1$H NMR and $^{13}$C NMR. $^1$H NMR: 7.85(d; J=8.2 Hz; 2Har.); 7.4(d; 2H; J=8.2 Hz; 2Har.); 7.15(d; 2H; J=2.9; H-imidazolyl); 5.4 (m; 1H; H2); 5.2 (m; 1H; H3); 4.95(dd; 1H; J=14.5, 3.5 Hz; H4a); 4.5(dd; 1H; J=14.5, 3.5 Hz; H4b) 4.3 (m; 2H; h1); 2.45(s; 3H; CH$_3$tosyl); 1.98(s; 6H; 2CH$_3$ac.). $^{13}$C NMR 169.4 (O$\underline{C}$OCH3); 146(Car.); 132(Car.); 130.1(CHar); 128.3(C-imidazolyl); 127.9(CH-imidazolyl); 127.4(CHar); 126.7(CH-imidazolyl); 69.3(C2, 3); 67.1(C1); 49.3(C4); 21.6(CH3tosyl); 20.5(CH3ac.).

EXAMPLE 12

Synthesis of ($^{18}$F)Fluoromisonidazole butanol analogue (Compound 1B)

This compound can be prepared from 1-(2'-Nitro-1'-imidazolyl)-2,3-O-acetyl-4-O-tosylbutanol, KRYPTOFIX® 222-fluoride complex in acetonitrile as described for ($^{18}$F) FMISO synthesis. The ($^{18}$F) fluoromisonidazole butanol analog is usable for PET tumor imaging.

EXAMPLE 13

Radiosynthesis of $^{131}$I Iodomisonidazole (Compound 1C)

5 mg of tosylmisonidazole was dissolved in 1 mL of acetone. Na$^{131}$I (1 mCi in borate buffer) was added. The reaction mixture was heated at 80° C. for 1 hour. Radio-thin layer chromatographic (TLC) analysis showed two peaks with Rf values of 0.01 and 0.72. The first peak was free Na$^{134}$I and the second peak was $^{131}$I-iodomisonidazole. Radio-TLC indicated the desired product has 45% yield. The pure product was obtained after hydrolysis and then passed through a silica gel column and eluted with ether:petroleum ether:triethylamine (1:1:10%). This compound is useful therapeutically.

EXAMPLE 14

Synthesis of (2'-nitro-1'-imidazolyl)-2,3-isopropylidene-4-tosylbutanol (Compound 10)

A mixture of 1,4-ditosyl-2,3-isopropylidene-D-threitol (ET) (0.47 g, 1 mmol), 2-nitroimidazole (0.1 g, 0.9 mmol), and cesium carbonate (0.29 g, 0.9 mmol) in 10 ml of dry dimethylformamide (DMF) was heated at 60° C. for 1 h. The reaction was then cooled and DMF was removed under reduced pressure. The residue was taken up in ethyl acetate and filtered. Removal of ethyl acetate in vacuo produced a yellow oil which was chromatographed on silica gel, eluted with petroleum ether/ethyl acetate (gradient form 10% to 70%) to afford a white solid (0.27 g, 0.63 mmol, 70% yield). The structure of the product was determined by $^1$H and $^{13}$C NMR and mass spectral data. HPLC showed the retention times of the title compound to be 12.45 min, and the ET compound to be 14.8 min (UV 254 nm, Brownlee C-18 5$\mu$ reverse phase column, 4.6×100 mm eluted with water/methanol, 0–80%, at a flow rate of 1.0 ml/min).

EXAMPLE 15

Radiosynthesis of [$^{18}$F]fluoroerythro-2-nitroimidazole (FETNIM) (COMPOUND 9)

[$^{18}$F]Fluoride was produced in the cyclotron facility (42 MeV, Cyclotron Corp., Berkeley, Calif.) at the University of Texas M.D. Anderson Cancer Center by proton irradiation of enriched $^{18}$O-water in a small-volume titanium target. The target was filled with 2 ml of [$^{18}$0] water. Aliquots containing 400–500 mCi of $^{18}$F activity after 1 hour beam time (12 $\mu$A current) was combined with KRYPTOFIX®-2,2,2 (26 mg)

and anhydrous potassium carbonate (4.6 mg), heated under reduced pressure to remove [$^{18}$O] water, and dried by azeotropic distillation with acetonitrile (3×1.5 mL). The tosyl analogue of 2-nitroimidazole (Compound 10, 20 mg), prepared from (Compound 10) was dissolved in acetonitrile (1.5 mL), added to the KRYPTOFIX®-fluoride complex, and then warmed at 95° C. for 10 min. After cooling, the reaction mixture was passed through a silica gel Sep-pak column (Whatman Lab, Clifton, N.J.) and eluted with ether (2×2.5 mL). The solvent was evaporated and the resulting mixture was hydrolyzed with 2N HCl (1 mL) at 105° C. for 10 min. The mixture was cooled under $N_2$ and neutralized with 2N NaOH (0.8 mL) and 1N $NaHCO_3$ (1 mL). The mixture was passed through a short alumina column, a C-18 Sep-Pak column, and a 0.22-$\mu$m Millipore filter, followed by eluting 6 mL of 10% ethanol/saline. A yield of 70–80 mCi of pure product was isolated (20–30% yield, decay corrected) with the end of bombardment (EOB) at 70 min. HPLC was performed on a Brownlee (5$\mu$ reverse phase) column, 4.6×100 mm, with water/methanol, 0×80%, using a flow rate of 1 mL/min. The no-carrier-added product corresponded to the retention time (3.11 min) of the unlabeled FETNIM under similar conditions. The retention time before hydrolysis of compound 9 was 8.94 min. The radiochemical purity was greater than 99%. Under the UV detector (254 nm), there were no other impurities. A radio-TLC scanner (Bioscan, Washington, DC) showed a retardation factor of 0.3 for the final product using a silica gel plate G/UV 254, 5×20 cm (Whatman, Anaspec, Mich.), eluted with chloroform:methanol (7:3), which corresponds to the unlabeled FETNIM. In addition, KRYPTOFIX®-2,2,2 was not visualized (developed in iodine chamber) on the silica gel-coated plate using 0.1% (v/v) triethylamine in methanol as an eluant. The specific activity of [$^{18}$F]FETNIM ranged from 1 to 2 Ci/$\mu$mol based upon UV and radioactivity detection of a sample of known mass and radioactivity.

EXAMPLE 16

PET Imaging Studies Using [$^{18}$F]FETNIM

PET imaging was performed with a positron camera (Positron Corporation, Houston, Tex.). The tomograph has a field-of-view of 42 cm on transverse and 12 cm on coronal planes. The axial resolution on the reconstructed plane is 1.2 cm. Twenty-one transaxial slices separated by 5.2 mm were reconstructed and displayed in standard uptake value (SUV) which measures the ratio of tissue radiotracer uptake to that of the whole body uptake for each scan.

Three male New Zealand white rabbits each weighing 3 kg were inoculated at a single site in the right buttock area with a 0.5 ml suspension of minced VX2 tumor fragments ($10^6$ cells/rabbit). The tumors are maintained through serial animal passage and are available from the Department of Veterinary Medicine (The University of Texas M.D. Anderson Cancer Center, Houston, Tex.). When the tumor size reached 2 cm by two weeks after inoculation, each rabbit was administered 4 mCi of [$^{18}$F]FETNIM. A 20 minute attenuation scan was performed with a 4 mCi $^{68}$Ge-ring source prior to tracer injection. Each rabbit was supine in the scanner so that the detector rings would span the entire lumbar region. Eight consecutive 10 minute scans were acquired. There was a 5 minute wait between scans for data transfer. The total number of counts collected per scan was in the range of 3–6 million.

Figure 7:
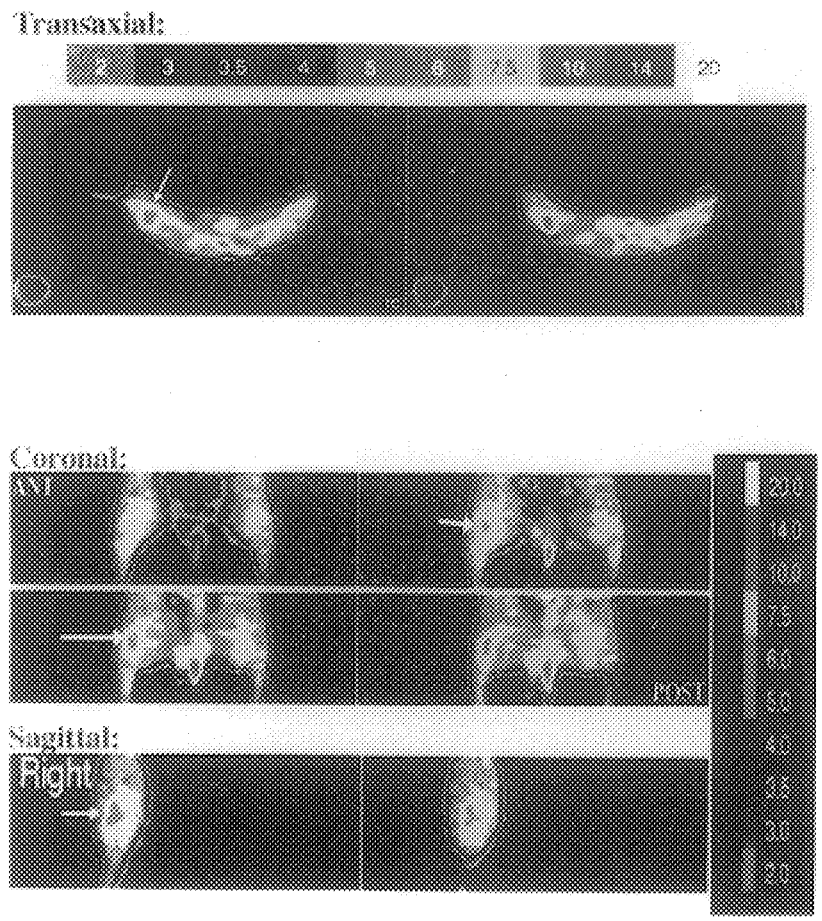
FIG. 7 shows the PET images of tumor bearing rabbits 1 hour post-injection with [$^{18}$F]FETNIM.

The coronal, transaxial and sagittal views of a PET image of a tumor-bearing rabbit 1 hour after administration of [$^{18}$F]FETNIM is shown in FIG. 7. The rabbit was scanned from cranial to caudal direction. The tumor can be visualized at one hour postinjection of [$^{18}$F]FETNIM. The SUV value of the tumor was greater than 10.

EXAMPLE 17

Autoradiographic studies of [$^{18}$F]FETNIM in tumor-bearing rats

Female Fischer 344 mammary tumor-bearing rats (n=3) after receiving [$^{18}$F]FETNIM (2 mCi, iv) were sacrificed at 1 h. To ascertain the metabolic and hypoxic character of the tumor, one rat was administered [$^{18}$F]fluorodeoxyglucose and another rat was given [$^{18}$F]fluoromisonidazole (2 mCi, iv). The rats were sacrificed at 1 hour postinjection. The rat body was fixed in a carboxymethyl cellulose (4%) block. The frozen body in a block was mounted to a cryostat (LKB 2250 cryo-microtome, Ijamsville, Md.) and 40 $\mu$m coronal sections were made. The section was freeze dried, then mounted on a x-ray film (X-Omat AR, Kodak, Rochester, N.Y.) for 24 hours.

Figure 8:
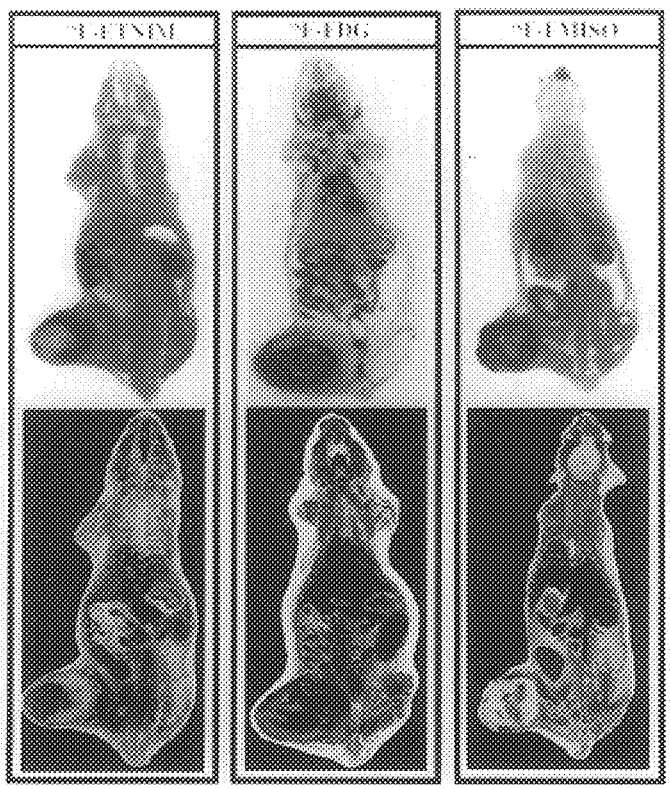
FIG. 8 shows the autoradiogram and photographic studies of mammary tumor bearing rats treated with [$^{18}$F]FETNIM, [$^{18}$F]FDG and [$^{18}$F]FMISO.

In vivo autoradiographic studies in mammary tumor-bearing rats indicated that the tumor could be visualized 1 hour postinjection. However, in the center region of the tumor, there was a lack of uptake of [$^{18}$F]FETNIM, suggesting tissue necrosis (FIG. 8). The necrotic region can be verified from the photograph. The autoradiogram of [$^{18}$F]FDG indicated that the tumor was metabolically active. The distribution of [$^{18}$F]FDG in a tumor-bearing rat was different from [$^{18}$F]FETNIM and [$^{18}$F]FMISO. The intestines and colon showed high uptake in [$^{18}$F]FETNIM and [$^{18}$F]FMISO. However, the medullary of the kidney area had higher uptake in the [$^{18}$F]FETNIM specimen.

EXAMPLE 18

Polar Graphic Oxygen Needle Probe Measurements

To confirm hypoxic tumors detected by imaging, intratumoral $pO_2$ measurements were performed using the Eppendorf computerized histographic system. Twenty to twenty-five $pO_2$ measurements along each of two to three linear tracks were performed at 0.4 mm intervals on each tumor (40–75 measurements in total). Tumor $pO_2$ measurements were conducted on 3 tumor-bearing rats and rabbits. Using an on-line computer system, the $pO_2$ measurements of each track were expressed as absolute values relative to the location of the measuring point along the track, and as the relative frequencies within a $pO_2$ histogram between 0 and 100 mmHg with a class width of 2.5 mm.

Intratumoral $pO_2$ measurement of the mammary tumors and VX2 tumors indicated that both tumor oxygen tensions ranged from 3.2 to 6.0 mmHg; the normal muscle oxygen tension was 30–40 mmHg. Both tumors are hypervascular in their viable region and hypovascular in their central region. Both tumor-bearing animal models are suitable for the evaluation of tumor hypoxia.

EXAMPLE 19

In Vivo Biodistribution of [$^{18}$F]FETNIM in Tumor-Bearing Rats

Female Fischer 344 rats (250–275 g) (Harlan, Inc., Indianapolis, Ind.) were inoculated with mammary tumor cells in the lumbar area using a 13762 tumor cell line (s.c. $10^5$ cells/rat). After 14 days, a tumor size of 1–2 cm was observed. Three groups of rats (N=3/group) were anesthetized with ketamine (10–15 mg/rat). The $^{18}$F-FETNIM reconstituted in 5% ethanol/saline was given to rats (10 μCi/rat, iv) and tissue distribution was conducted at 1h, 2h and 4h intervals. The tissues were excised, weighed and counted for radioactivity. The percent of injected dose per gram of tissue weight was determined.

Figure 9:
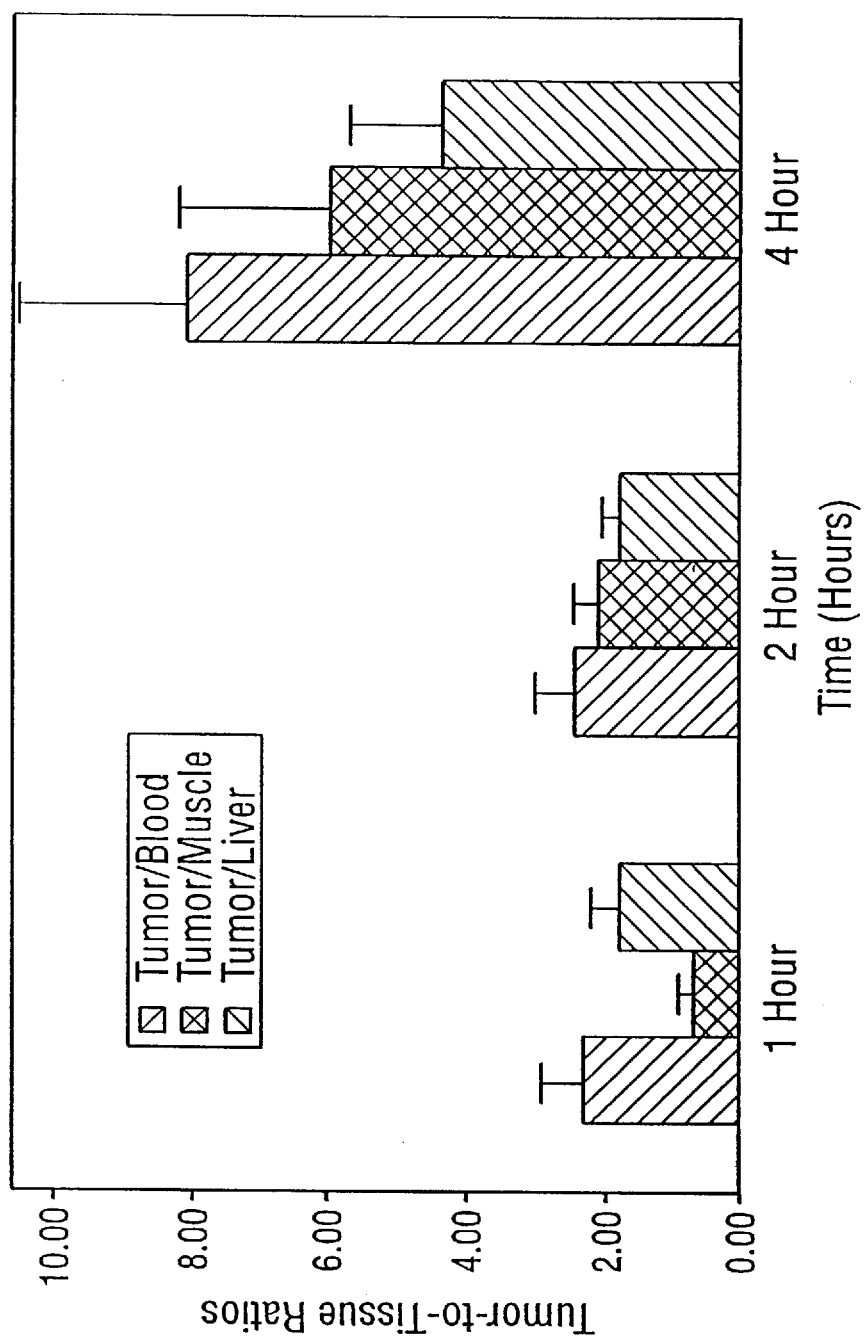
FIG. 9 is a histogram showing tumor-to-tissue ratios of [$^{18}$F]FETNIM in tumor bearing rats.

The tissue distribution of [$^{18}$F]FETNIM in the tumor-bearing rats is shown in Table 2. Bone had high affinity for ionic fluoride, the bone uptake value did not alter, suggesting the in vivo stability of [$^{18}$F]FETNIM. The tumor/muscle, tumor/blood and tumor/liver count density ratios showed increases with time (FIG. 9), the tumor-to-blood count density being 8.0±2.42 at 4 hour postinjection of [$^{18}$F]FETNIM. This increased tumor-to-background ratio suggests that [$^{18}$F]FETNIM has the potential to detect tumor hypoxia.

TABLE 2

Biodistribution of [$^{18}$F] Fluoroerythronitroimidazole in Tumor-Bearing Rats[1]
(Percent of Injected Dose/Gram Weight; N = 3/Time Interval)

| TIME | 1 HOUR | 2 HOUR | 4 HOUR |
| --- | --- | --- | --- |
| BLOOD | 0.3493 ± 0.02173 | 0.1950 ± 0.02828 | 0.0993 ± 0.01266 |
| LUNG | 0.3577 ± 0.00723 | 0.2107 ± 0.05713 | 0.1027 ± 0.02122 |
| LIVER | 0.4530 ± 0.01493 | 0.3123 ± 0.08225 | 0.1843 ± 0.02458 |
| SPLEEN | 0.3183 ± 0.02011 | 0.2013 ± 0.05918 | 0.0953 ± 0.01401 |
| KIDNEY | 0.8860 ± 0.00424 | 0.5145 ± 0.02334 | 0.4663 ± 0.06866 |
| BONE | 0.2570 ± 0.14001 | 0.0810 ± 0.00424 | 0.0753 ± 0.01570 |
| MUSCLE | 1.2600 ± 0.08627 | 0.2670 ± 0.09036 | 0.1377 ± 0.01893 |
| TUMOR | 0.7957 ± 0.20358 | 0.5516 ± 0.15818 | 0.8113 ± 0.33773 |
| TUMOR/BLOOD | 2.2900 ± 0.59940 | 2.4100 ± 0.56719 | 8.0200 ± 2.42000 |
| TUMOR/MUSCLE | 0.6602 ± 0.26659 | 2.1100 ± 0.34679 | 5.9200 ± 2.24000 |
| TUMOR/LIVER | 1.7600 ± 0.44151 | 1.7700 ± 0.25608 | 4.3300 ± 1.31000 |

[1]13762 cell line was inoculated to rats (s.c. 10$^5$ cells/rat). When tumor size reached 1–2 cm, each rat was administered 10μCi tracer.

REFERENCES

The following references are incorporated by reference herein in pertinent part for the reasons cited in the above text.

Benbouzid, et al., *Fat. Sci. Technol.* 1988, 90(8), 292–295.
Brown JM, Workman P. *Radiat Res* (1980), 82:171–190.
Bush RS, Jenkins RDT, Allt WEC, Beale FA, Bena H, Dembo AJ, Pringle JF. *Br J Cancer.* (1978), 37(Suppl. III):302–306.
Cherif A, Yang DJ, Tansey W, Kim EE, Wallace S. *Pharm Res* (1994), 11:466–469.
Clifford KH, Briggs RL, Stone HB. *J Natl Cancer Inst* (1965), 36:965–974.
Dische S. *Int J Radiat Oncol Biol Phys* (1991), 20:147–152.
Gatenby, R. A. et al., *Int. J. Radiat. Oncol. Biol. Phy.,* 1988, 14, 831–838.
Gray LH, Conger AD, Ebert M, Hornsey S, Scott OCA. *Br J Cancer* (1953), 26:638–642. Grierson, J. R. et al., *J. Nucl. Med.* 1989, 30, 343–350.
Hall E. J. ed., Radiosensitizers and Bioreductive drugs *In:* Radiobiology for the Radiologist. JB Lippincott Company, Philadelphia, Pa. 1994, pp. 165–181.
Hall, E. J. "The oxygen effect and reoxygenation," *In:* Radiobiology for the Radiobiologist, Hall, E. J. Ed.; Lippincott Co.; Philadelphia, Pa., 1988; pp. 137–160.
Hockel M, Knoop C, Schlenger K, Vorndrant B, Baubmann E, Mitze M, Knapstein PG, Vaupel P. Radio Oncol (1993), 26(1):45–50.
Hoffer, et al., J. Med. Chem. 17, 1019–1020, 1974.
Hwang, D. R. et al., *Int. J. Rad. Appl. Instrum. A.* 1989, 40, 117–126.
Jerabek, P. A. et al., *App. Radiat. Isot.* 1986, 37, 599–605.
Kayama, T. et al., *Neurosurg.* 1991, 4, 55–59.
Koh, W-J. et al., *Int. J. Radiat. Oncol. Biol.* 1992, 22, 199–212.
Koh W-J, Rasey JS, Evans ML, et al. *Int J Radiat Oncol Biol Phy* (1992), 22:199–212.
Lim, J. L. et al. *9th International Symposium of Radiopharmaceutical Chemistry,* Paris, France, Apr. 6, 1992.
Maor, M. H., et al., *Int. J. Radiat. Oncol. Biol. Phy.* 1981, 7, 155–159.
Martin GV, Caldwell JH, Rasey JS, Grunbaum Z, Cerqueia M, Krohn KA. *J Nucl Med* (1989), 30:194–201.
Martin DF, Porter EA, Fischer JJ, Rockwell S. *Radiat Res* (1987), 112:45–53.
Martin DF, Porter EA, Rockwell S, Fischer JJ. *Int J Radiat Oncol Biol Phy* (1987), 13:747–751.
Martin, G. V. et al., *J. Nucl. Med.* 1989, 30, 194–201.
McNeill, et al., *Int. J. Radiation Oncol. Biol. Phys.,* 12, 1067–1070, 1986.
Morton JD, Porter E, Yabuki H, Nath R, Rockwell S. *Radiat Res* (1990), 124:178–182.
Morton JD, Yabuki H, Porter E, Rockwell S, Nath R. *Radiat Res* (1989), 119:478–488.
Moulder JE, Martin GV. *Radiat Res* (1984), 98:536–548.
Moulder, J. E. et al., *Int. J. Radiat. Oncol. Biol. Phys.,* 1984, 10, 695–712.
Peters LJ, Withers HR, Thames HD, Fletcher GH. *Int J Radiat Oncol Biol Phys* (1982), 8:101–108.
Powers, W. E. et al., *Nature,* 1963, 197, 710–711.
Rasey JS, Nelson NJ, Chin L, Evans ML, Grunbaum Z. *Radiat Res* (1990), 122:301–308.
Rasey JS, Koh WJ, Grieson JR, Grunbaum Z, Krohn KA. *Int J Radiat Oncol Biol Phys* (1989), 17:985–991.
Valk PET, Mathis CA, Prados MD, Gilbert JC, Budinger TF. *J Nucl Med* (1992), 33:2133–2137.

It is understood that equivalents of the following claims involve simple substitution of analogous chemicals and methods well known to those of skill in the art.

We claim:

1. 1-(2'-Nitro-1'-imidazolyl)-2-O-acetyl-3-O-tosylpropanol.

2. A method for preparing 1-(2'-nitro-1'-imidazolyl)-2-O-acetyl-3-O-tosylpropanol comprising reacting glycerol-1,3-ditosylate-2-O-acetylate with 2-nitroimidazole.

3. The method of claim 2 where the reacting is in dimethylformamide.

4. The method of claim 2 where the reacting is in the presence of cesium carbonate.

5. The method of claim 2 where the reacting is at about 50° C. for about 1 hour.

* * * * *